(12) United States Patent
Biberger et al.

(10) Patent No.: US 9,180,423 B2
(45) Date of Patent: Nov. 10, 2015

(54) HIGHLY TURBULENT QUENCH CHAMBER

(75) Inventors: Maximilian A. Biberger, Scottsdale, AZ (US); Frederick P. Layman, Carefree, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 1880 days.

(21) Appl. No.: 12/151,935

(22) Filed: May 8, 2008

(65) Prior Publication Data

US 2008/0277267 A1 Nov. 13, 2008

Related U.S. Application Data

(60) Provisional application No. 60/928,946, filed on May 11, 2007.

(51) Int. Cl.
*B01J 19/08* (2006.01)
*B01J 19/00* (2006.01)
(Continued)

(52) U.S. Cl.
CPC .............. *B01J 19/0013* (2013.01); *B01J 25/00* (2013.01); *B01J 25/02* (2013.01); *B22F 9/12* (2013.01); *F28D 15/00* (2013.01); *F28F 27/00* (2013.01); *B22F 2999/00* (2013.01); *F28D 7/024* (2013.01); *F28D 7/08* (2013.01); *Y10S 623/92* (2013.01); *Y10S 623/923* (2013.01);
(Continued)

(58) Field of Classification Search
CPC ................. B01J 2219/0871; B01J 2219/0847; B01J 2219/1239
USPC ....................... 422/186, 906, 907; 204/157.15
See application file for complete search history.

(56) References Cited

U.S. PATENT DOCUMENTS 2,021,936 A 11/1935 Johnstone
2,284,554 A 5/1942 Beyerstedt
(Continued)

FOREIGN PATENT DOCUMENTS

CN 1647858 A 8/2005
CN 101011664 A 8/2007
(Continued)

OTHER PUBLICATIONS

Nagai, Yasutaka, et al., "Sintering Inhibition Mechanism of Platinum Supported on Ceria-based Oxide and Pt-oxide-support Interaction," Journal of Catalysis 242 (2006), pp. 103-109, Jul. 3, 2006, Elsevier.
(Continued)

*Primary Examiner* — Natalia Levkovich
(74) *Attorney, Agent, or Firm* — Morrison & Foerster LLP (57) ABSTRACT

An apparatus for cooling a reactive mixture, comprising: a reactor configured to form the reactive mixture; a quench chamber comprising a frusto-conical body having a wide end, a narrow end, and a quench region formed between the wide and narrow end, wherein the quench chamber is configured to receive the reactive mixture from the plasma reactor through a reactive mixture inlet into the quench region, to receive a conditioning fluid through at least one fluid inlet, and to flow the conditioning fluid into the quench region, wherein the frusto-conical body is configured to produce a turbulent flow within the quench region with the flow of the conditioning fluid into the quench region, thereby promoting the quenching of the reactive mixture to form a cooled gas-particle mixture; and a suction generator configured to force the cooled gas-particle mixture out of the quench chamber.

16 Claims, 5 Drawing Sheets

(51) Int. Cl.
  B22F 9/12    (2006.01)
  F28D 15/00   (2006.01)
  F28F 27/00   (2006.01)
  B01J 25/00   (2006.01)
  B01J 25/02   (2006.01)
  F28D 7/02    (2006.01)
  F28D 7/08    (2006.01)

(52) U.S. Cl.
  CPC ..... Y10T 137/0391 (2015.04); Y10T 137/2076 (2015.04); Y10T 156/15 (2015.01)

(56) References Cited

U.S. PATENT DOCUMENTS

| | | | |
|---|---|---|---|
| 2,419,042 A | 4/1947 | Todd | 202/205 |
| 2,519,531 A | 8/1950 | Worn | 230/95 |
| 2,562,753 A | 7/1951 | Trost | |
| 2,689,780 A | 9/1954 | Rice | 23/106 |
| 3,001,402 A | 9/1961 | Koblin | 73/421.5 |
| 3,042,511 A | 7/1962 | Reding, Jr. | |
| 3,067,025 A | 12/1962 | Chisholm | |
| 3,145,287 A | 8/1964 | Siebein et al. | |
| 3,178,121 A | 4/1965 | Wallace, Jr. | |
| 3,179,782 A | 4/1965 | Matvay | |
| 3,181,947 A | 5/1965 | Vordahl | |
| 3,235,700 A | 2/1966 | Mondain-Monval et al. | |
| 3,313,908 A | 4/1967 | Unger et al. | |
| 3,387,110 A | 6/1968 | Wendler et al. | |
| 3,401,465 A | 9/1968 | Larwill | |
| 3,450,926 A | 6/1969 | Kiernan | |
| 3,457,788 A | 7/1969 | Miyajima | 73/422 |
| 3,520,656 A | 7/1970 | Yates et al. | |
| 3,537,513 A | 11/1970 | Austin et al. | 165/70 |
| 3,552,653 A | 1/1971 | Inoue | |
| 3,617,358 A | 11/1971 | Dittrich | |
| 3,667,111 A | 6/1972 | Chartet | |
| 3,730,827 A | 5/1973 | Matchen et al. | |
| 3,741,001 A | 6/1973 | Fletcher et al. | 73/28 |
| 3,752,172 A | 8/1973 | Cohen et al. | |
| 3,761,360 A | 9/1973 | Auvil et al. | |
| 3,774,442 A | 11/1973 | Gustavsson | 73/28 |
| 3,804,034 A | 4/1974 | Stiglich, Jr. | |
| 3,830,756 A | 8/1974 | Sanchez et al. | |
| 3,857,744 A | 12/1974 | Moss | |
| 3,871,448 A | 3/1975 | Vann et al. | |
| 3,892,882 A | 7/1975 | Guest et al. | |
| 3,914,573 A | 10/1975 | Muehlberger | |
| 3,959,094 A | 5/1976 | Steinberg | |
| 3,959,420 A | 5/1976 | Geddes et al. | 261/112 |
| 3,969,482 A | 7/1976 | Teller | |
| 4,008,620 A | 2/1977 | Narato et al. | 73/421.5 A |
| 4,018,388 A | 4/1977 | Andrews | |
| 4,021,021 A | 5/1977 | Hall et al. | |
| 4,127,760 A | 11/1978 | Meyer et al. | |
| 4,139,497 A | 2/1979 | Castor et al. | |
| 4,146,654 A | 3/1979 | Guyonnet | |
| 4,157,316 A | 6/1979 | Thompson et al. | |
| 4,171,288 A | 10/1979 | Keith et al. | |
| 4,174,298 A | 11/1979 | Antos | |
| 4,189,925 A | 2/1980 | Long | |
| 4,227,928 A | 10/1980 | Wang | |
| 4,248,387 A | 2/1981 | Andrews | |
| 4,253,917 A | 3/1981 | Wang | |
| 4,260,649 A | 4/1981 | Dension et al. | |
| 4,284,609 A | 8/1981 | deVries | |
| 4,315,874 A | 2/1982 | Ushida et al. | |
| 4,326,492 A | 4/1982 | Leibrand, Sr. et al. | |
| 4,344,779 A | 8/1982 | Isserlis | |
| 4,369,167 A | 1/1983 | Weir | |
| 4,388,274 A | 6/1983 | Rourke et al. | |
| 4,419,331 A | 12/1983 | Montalvo | |
| 4,431,750 A | 2/1984 | McGinnis et al. | |
| 4,436,075 A | 3/1984 | Campbell et al. | 123/557 |
| 4,440,733 A | 4/1984 | Lawson et al. | |
| 4,458,138 A | 7/1984 | Adrian et al. | |
| 4,459,327 A | 7/1984 | Wang | |
| 4,505,945 A | 3/1985 | Dubust et al. | |
| 4,506,136 A | 3/1985 | Smyth et al. | |
| 4,513,149 A | 4/1985 | Gray et al. | |
| 4,523,981 A | 6/1985 | Ang et al. | |
| 4,545,872 A | 10/1985 | Sammells et al. | |
| RE32,244 E | 9/1986 | Andersen | |
| 4,609,441 A | 9/1986 | Frese, Jr. et al. | |
| 4,610,857 A | 9/1986 | Ogawa et al. | |
| 4,616,779 A | 10/1986 | Serrano et al. | |
| 4,723,589 A | 2/1988 | Iyer et al. | |
| 4,731,517 A | 3/1988 | Cheney | |
| 4,751,021 A | 6/1988 | Mollon et al. | |
| 4,764,283 A | 8/1988 | Ashbrook et al. | |
| 4,765,805 A | 8/1988 | Wahl et al. | |
| 4,780,591 A | 10/1988 | Bernecki et al. | |
| 4,824,624 A | 4/1989 | Palicka et al. | 264/67 |
| 4,836,084 A | 6/1989 | Vogelesang et al. | |
| 4,855,505 A | 8/1989 | Koll | |
| 4,866,240 A | 9/1989 | Webber | |
| 4,877,937 A | 10/1989 | Müller | |
| 4,885,038 A | 12/1989 | Anderson et al. | |
| 4,921,586 A | 5/1990 | Molter | |
| 4,970,364 A | 11/1990 | Müller | |
| 4,982,050 A | 1/1991 | Gammie et al. | |
| 4,983,555 A | 1/1991 | Roy et al. | 501/120 |
| 4,987,033 A | 1/1991 | Abkowitz et al. | 428/469 |
| 5,006,163 A | 4/1991 | Benn et al. | |
| 5,015,863 A | 5/1991 | Takeshima et al. | |
| 5,041,713 A | 8/1991 | Weidman | |
| 5,043,548 A | 8/1991 | Whitney et al. | 219/121.84 |
| 5,070,064 A | 12/1991 | Hsu et al. | |
| 5,073,193 A | 12/1991 | Chaklader et al. | 75/346 |
| 5,133,190 A | 7/1992 | Abdelmalek | |
| 5,151,296 A | 9/1992 | Tokunaga | |
| 5,157,007 A | 10/1992 | Domesle et al. | |
| 5,187,140 A | 2/1993 | Thorsteinson et al. | |
| 5,192,130 A | 3/1993 | Endo et al. | |
| 5,217,746 A | 6/1993 | Lenling et al. | |
| 5,225,656 A | 7/1993 | Frind | |
| 5,230,844 A | 7/1993 | Macaire et al. | |
| 5,233,153 A | 8/1993 | Coats | |
| 5,269,848 A | 12/1993 | Nakagawa | |
| 5,294,242 A | 3/1994 | Zurecki et al. | |
| 5,330,945 A | 7/1994 | Beckmeyer et al. | |
| 5,338,716 A | 8/1994 | Triplett et al. | |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,436,080 A | 7/1995 | Inoue et al. | |
| 5,439,865 A | 8/1995 | Abe et al. | |
| 5,442,153 A | 8/1995 | Marantz et al. | |
| 5,452,854 A | 9/1995 | Keller | |
| 5,460,701 A * | 10/1995 | Parker et al. | 204/164 |
| 5,464,458 A | 11/1995 | Yamamoto | |
| 5,485,941 A | 1/1996 | Guyomard et al. | |
| 5,486,675 A | 1/1996 | Taylor et al. | |
| 5,489,449 A | 2/1996 | Umeya et al. | |
| 5,534,149 A | 7/1996 | Birkenbeil et al. | |
| 5,534,270 A | 7/1996 | De Castro | |
| 5,543,173 A | 8/1996 | Horn, Jr. et al. | |
| 5,553,507 A | 9/1996 | Basch et al. | 73/863.01 |
| 5,558,771 A | 9/1996 | Hagen et al. | |
| 5,562,966 A | 10/1996 | Clarke et al. | |
| 5,582,807 A | 12/1996 | Liao et al. | |
| 5,596,973 A | 1/1997 | Grice | |
| 5,611,896 A | 3/1997 | Swanepoel et al. | 204/169 |
| 5,630,322 A | 5/1997 | Heilmann et al. | |
| 5,652,304 A | 7/1997 | Mizrahi | |
| 5,714,644 A | 2/1998 | Irgang et al. | |
| 5,723,027 A | 3/1998 | Serole | |
| 5,723,187 A | 3/1998 | Popoola et al. | |
| 5,726,414 A | 3/1998 | Kitahashi et al. | |
| 5,733,662 A | 3/1998 | Bogachek | |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |

(56) References Cited

U.S. PATENT DOCUMENTS

| | | | |
|---|---|---|---|
| 5,804,155 A | 9/1998 | Farrauto et al. | |
| 5,811,187 A | 9/1998 | Anderson et al. | 428/403 |
| 5,837,959 A | 11/1998 | Muehlberger et al. | |
| 5,851,507 A | 12/1998 | Pirzada et al. | |
| 5,853,815 A | 12/1998 | Muehlberger | 427/446 |
| 5,858,470 A | 1/1999 | Bernecki et al. | |
| 5,884,473 A | 3/1999 | Noda et al. | |
| 5,905,000 A | 5/1999 | Yadav et al. | 429/33 |
| 5,928,806 A | 7/1999 | Olah et al. | |
| 5,935,293 A | 8/1999 | Detering et al. | 75/10.19 |
| 5,973,289 A | 10/1999 | Read et al. | |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,004,620 A | 12/1999 | Camm | |
| 6,012,647 A | 1/2000 | Ruta et al. | 239/132.1 |
| 6,033,781 A | 3/2000 | Brotzman, Jr. et al. | 428/405 |
| 6,045,765 A | 4/2000 | Nakatsuji et al. | |
| 6,059,853 A | 5/2000 | Coombs | 75/332 |
| 6,066,587 A | 5/2000 | Kurokawa et al. | |
| 6,084,197 A | 7/2000 | Fusaro, Jr. | |
| 6,093,306 A | 7/2000 | Hanrahan et al. | |
| 6,093,378 A | 7/2000 | Deeba et al. | |
| 6,102,106 A | 8/2000 | Manning et al. | 165/76 |
| 6,117,376 A | 9/2000 | Merkel | |
| 6,140,539 A | 10/2000 | Sander et al. | |
| 6,168,694 B1 | 1/2001 | Huang et al. | |
| 6,190,627 B1 | 2/2001 | Hoke et al. | |
| 6,213,049 B1 | 4/2001 | Yang | |
| 6,214,195 B1 | 4/2001 | Yadav et al. | 205/334 |
| 6,228,904 B1 | 5/2001 | Yadav et al. | 523/214 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,322,756 B1 | 11/2001 | Arno et al. | |
| 6,342,465 B1 | 1/2002 | Klein et al. | |
| 6,344,271 B1 | 2/2002 | Yadav et al. | 428/402 |
| 6,362,449 B1 | 3/2002 | Hadidi et al. | |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,399,030 B1 | 6/2002 | Nolan | |
| 6,409,851 B1 | 6/2002 | Sethuram et al. | 148/565 |
| 6,413,781 B1 | 7/2002 | Geis et al. | |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,475,951 B1 | 11/2002 | Domesle et al. | |
| 6,488,904 B1 | 12/2002 | Cox et al. | |
| 6,491,423 B1 | 12/2002 | Skibo et al. | |
| 6,506,995 B1 | 1/2003 | Fusaro, Jr. et al. | |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,548,445 B1 | 4/2003 | Buysch et al. | |
| 6,554,609 B2 | 4/2003 | Yadav et al. | 432/9 |
| 6,562,304 B1 | 5/2003 | Mizrahi | |
| 6,562,495 B2 | 5/2003 | Yadav et al. | 429/12 |
| 6,569,393 B1 | 5/2003 | Hoke et al. | |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,579,446 B1 | 6/2003 | Teran et al. | |
| 6,596,187 B2 | 7/2003 | Coll et al. | |
| 6,603,038 B1 | 8/2003 | Hagemeyer et al. | |
| 6,607,821 B2 | 8/2003 | Yadav et al. | 428/323 |
| 6,610,355 B2 | 8/2003 | Yadav et al. | 427/115 |
| 6,623,559 B2 | 9/2003 | Huang | |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,706,660 B2 | 3/2004 | Park | |
| 6,710,207 B2 | 3/2004 | Bogan, Jr. et al. | |
| 6,713,176 B2 | 3/2004 | Yadav et al. | 428/402 |
| 6,716,525 B1 | 4/2004 | Yadav et al. | 428/402 |
| 6,744,006 B2 | 6/2004 | Johnson et al. | |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,841,509 B1 | 1/2005 | Hwang et al. | |
| 6,855,410 B2 | 2/2005 | Buckley | |
| 6,855,426 B2 | 2/2005 | Yadav | 428/403 |
| 6,855,749 B1 | 2/2005 | Yadav et al. | 523/105 |
| 6,858,170 B2 | 2/2005 | Van Thillo et al. | |
| 6,886,545 B1 | 5/2005 | Holm | |
| 6,891,319 B2 | 5/2005 | Dean et al. | |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,065 B2 | 7/2005 | Zhou et al. | |
| 6,919,527 B2 | 7/2005 | Boulos et al. | 219/121.52 |
| 6,933,331 B2 | 8/2005 | Yadav et al. | 523/210 |
| 6,972,115 B1 | 12/2005 | Ballard | |
| 6,986,877 B2 | 1/2006 | Takikawa et al. | 423/447.3 |
| 6,994,837 B2 | 2/2006 | Boulos et al. | 423/613 |
| 7,007,872 B2 | 3/2006 | Yadav et al. | 241/1 |
| 7,022,305 B2 | 4/2006 | Drumm et al. | |
| 7,052,777 B2 | 5/2006 | Brotzman, Jr. et al. | 428/570 |
| 7,073,559 B2 | 7/2006 | O'Larey et al. | 164/76.1 |
| 7,074,364 B2 | 7/2006 | Jähn et al. | |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflang | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,172,790 B2 | 2/2007 | Koulik et al. | |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | |
| 7,255,498 B2 | 8/2007 | Bush et al. | |
| 7,265,076 B2 | 9/2007 | Taguchi et al. | |
| 7,282,167 B2 | 10/2007 | Carpenter | |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 7,402,899 B1 | 7/2008 | Whiting et al. | |
| 7,417,008 B2 | 8/2008 | Richards et al. | |
| 7,494,527 B2 | 2/2009 | Jurewicz et al. | |
| 7,507,495 B2 | 3/2009 | Wang et al. | |
| 7,517,826 B2 | 4/2009 | Fujdala et al. | |
| 7,534,738 B2 | 5/2009 | Fujdala et al. | |
| 7,541,012 B2 | 6/2009 | Yeung et al. | |
| 7,541,310 B2 | 6/2009 | Espinoza et al. | |
| 7,557,324 B2 | 7/2009 | Nylen et al. | |
| 7,572,315 B2 | 8/2009 | Boulos et al. | |
| 7,576,029 B2 | 8/2009 | Saito et al. | |
| 7,576,031 B2 | 8/2009 | Beutel et al. | |
| 7,604,843 B1 | 10/2009 | Robinson et al. | |
| 7,611,686 B2 | 11/2009 | Alekseeva et al. | |
| 7,615,097 B2 | 11/2009 | McKechnie et al. | |
| 7,618,919 B2 | 11/2009 | Shimazu et al. | |
| 7,622,693 B2 | 11/2009 | Foret | |
| 7,632,775 B2 | 12/2009 | Zhou et al. | |
| 7,635,218 B1 | 12/2009 | Lott | |
| 7,674,744 B2 | 3/2010 | Shiratori et al. | |
| 7,678,419 B2 | 3/2010 | Kevwitch et al. | |
| 7,704,369 B2 | 4/2010 | Olah et al. | |
| 7,709,411 B2 | 5/2010 | Zhou et al. | |
| 7,709,414 B2 | 5/2010 | Fujdala et al. | |

(56) References Cited

U.S. PATENT DOCUMENTS

| | | |
|---|---|---|
| 7,745,367 B2 | 6/2010 | Fujdala et al. |
| 7,750,265 B2 | 7/2010 | Belashchenko et al. |
| 7,759,279 B2 | 7/2010 | Shiratori et al. |
| 7,759,281 B2 | 7/2010 | Kezuka et al. |
| 7,803,210 B2 | 9/2010 | Sekine et al. |
| 7,842,515 B2 | 11/2010 | Zou et al. |
| 7,851,405 B2 | 12/2010 | Wakamatsu et al. |
| 7,874,239 B2 | 1/2011 | Howland |
| 7,875,573 B2 | 1/2011 | Beutel et al. |
| 7,897,127 B2 | 3/2011 | Layman et al. |
| 7,902,104 B2 | 3/2011 | Kalck |
| 7,905,942 B1 | 3/2011 | Layman |
| 7,935,655 B2 | 5/2011 | Tolmachev |
| 8,003,020 B2 | 8/2011 | Jankowiak et al. |
| 8,051,724 B1 | 11/2011 | Layman et al. |
| 8,076,258 B1 | 12/2011 | Biberger |
| 8,080,494 B2 | 12/2011 | Yasuda et al. |
| 8,089,495 B2 | 1/2012 | Keller |
| 8,129,654 B2 | 3/2012 | Lee et al. |
| 8,142,619 B2 | 3/2012 | Layman et al. |
| 8,168,561 B2 | 5/2012 | Virkar |
| 8,173,572 B2 | 5/2012 | Feaviour |
| 8,211,392 B2 | 7/2012 | Grubert et al. |
| 8,258,070 B2 | 9/2012 | Fujdala et al. |
| 8,278,240 B2 | 10/2012 | Tange et al. |
| 8,294,060 B2 | 10/2012 | Mohanty et al. |
| 8,309,489 B2 | 11/2012 | Roldan Cuenya et al. |
| 8,349,761 B2 | 1/2013 | Xia et al. |
| 8,404,611 B2 | 3/2013 | Nakamura et al. |
| 8,470,112 B1 | 6/2013 | Biberger |
| 8,507,401 B1 | 8/2013 | Biberger et al. |
| 8,507,402 B1 | 8/2013 | Biberger et al. |
| 8,524,631 B2 | 9/2013 | Biberger |
| 8,545,652 B1 | 10/2013 | Biberger |
| 8,557,727 B2 | 10/2013 | Yin et al. |
| 8,574,408 B2 | 11/2013 | Layman |
| 8,574,520 B2 | 11/2013 | Koplin et al. |
| 8,575,059 B1 | 11/2013 | Biberger et al. |
| 8,604,398 B1 | 12/2013 | Layman |
| 8,652,992 B2 | 2/2014 | Yin et al. |
| 8,668,803 B1 | 3/2014 | Biberger |
| 8,669,202 B2 | 3/2014 | van den Hoek et al. |
| 8,679,433 B2 | 3/2014 | Yin et al. |
| 8,821,786 B1 | 9/2014 | Biberger |
| 8,828,328 B1 | 9/2014 | Leamon et al. |
| 8,859,035 B1 | 10/2014 | Leamon |
| 8,877,357 B1 | 11/2014 | Biberger |
| 8,893,651 B1 | 11/2014 | Biberger et al. |
| 8,906,498 B1 | 12/2014 | Biberger |
| 8,932,514 B1 | 1/2015 | Yin et al. |
| 8,992,820 B1 | 3/2015 | Yin et al. |
| 2001/0004009 A1 | 6/2001 | MacKelvie |
| 2001/0042802 A1 | 11/2001 | Youds |
| 2001/0055554 A1 | 12/2001 | Hoke et al. |
| 2002/0018815 A1 | 2/2002 | Sievers et al. |
| 2002/0068026 A1 | 6/2002 | Murrell et al. |
| 2002/0071800 A1 | 6/2002 | Hoke et al. |
| 2002/0079620 A1 | 6/2002 | DuBuis et al. ............ 264/328.14 |
| 2002/0100751 A1 | 8/2002 | Carr |
| 2002/0102674 A1 | 8/2002 | Anderson |
| 2002/0131914 A1 | 9/2002 | Sung |
| 2002/0143417 A1 | 10/2002 | Ito et al. |
| 2002/0168466 A1 | 11/2002 | Tapphorn et al. |
| 2002/0182735 A1 | 12/2002 | Kibby et al. |
| 2002/0183191 A1 | 12/2002 | Faber et al. |
| 2002/0192129 A1 | 12/2002 | Shamouilian et al. |
| 2003/0036786 A1 | 2/2003 | Duren et al. .................. 607/96 |
| 2003/0042232 A1 | 3/2003 | Shimazu |
| 2003/0047617 A1 | 3/2003 | Shanmugham et al. |
| 2003/0066800 A1 | 4/2003 | Saim et al. |
| 2003/0085663 A1 | 5/2003 | Horsky |
| 2003/0102099 A1 | 6/2003 | Yadav et al. |
| 2003/0108459 A1 | 6/2003 | Wu et al. .................. 422/186.04 |
| 2003/0110931 A1 | 6/2003 | Aghajanian et al. |
| 2003/0129098 A1 | 7/2003 | Endo et al. |
| 2003/0139288 A1 | 7/2003 | Cai et al. |
| 2003/0143153 A1 | 7/2003 | Boulos et al. |
| 2003/0172772 A1 | 9/2003 | Sethuram et al. |
| 2003/0223546 A1 | 12/2003 | McGregor et al. ............ 378/143 |
| 2004/0009118 A1 | 1/2004 | Phillips et al. |
| 2004/0023302 A1 | 2/2004 | Archibald et al. |
| 2004/0023453 A1 | 2/2004 | Xu et al. |
| 2004/0077494 A1 | 4/2004 | LaBarge et al. |
| 2004/0103751 A1 | 6/2004 | Joseph et al. ................ 75/10.19 |
| 2004/0109523 A1 | 6/2004 | Singh et al. |
| 2004/0119064 A1 | 6/2004 | Narayan et al. |
| 2004/0127586 A1 | 7/2004 | Jin et al. |
| 2004/0129222 A1 | 7/2004 | Nylen et al. |
| 2004/0166036 A1 | 8/2004 | Chen et al. |
| 2004/0167009 A1 | 8/2004 | Kuntz et al. ................. 501/95.2 |
| 2004/0176246 A1 | 9/2004 | Shirk et al. |
| 2004/0208805 A1 | 10/2004 | Fincke et al. |
| 2004/0213998 A1 | 10/2004 | Hearley et al. |
| 2004/0235657 A1 | 11/2004 | Xiao et al. |
| 2004/0238345 A1 | 12/2004 | Koulik et al. |
| 2004/0251017 A1 | 12/2004 | Pillion et al. ................. 165/289 |
| 2004/0251241 A1 | 12/2004 | Blutke et al. |
| 2005/0000321 A1 | 1/2005 | O'Larey et al. ................. 75/952 |
| 2005/0000950 A1 | 1/2005 | Schroder et al. ......... 219/121.59 |
| 2005/0058797 A1 | 3/2005 | Sen et al. |
| 2005/0066805 A1 | 3/2005 | Park et al. |
| 2005/0070431 A1 | 3/2005 | Alvin et al. |
| 2005/0077034 A1 | 4/2005 | King .............................. 165/163 |
| 2005/0097988 A1 | 5/2005 | Kodas et al. .................... 75/332 |
| 2005/0106865 A1 | 5/2005 | Chung et al. |
| 2005/0133121 A1 | 6/2005 | Subramanian et al. |
| 2005/0153069 A1 | 7/2005 | Tapphorn et al. |
| 2005/0163673 A1 | 7/2005 | Johnson et al. |
| 2005/0199739 A1 | 9/2005 | Kuroda et al. |
| 2005/0211018 A1 | 9/2005 | Jurewicz et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. ..................... 435/7.1 |
| 2005/0240069 A1 | 10/2005 | Polverejan et al. ............ 585/444 |
| 2005/0258766 A1 | 11/2005 | Kim ........................ 315/111.21 |
| 2005/0274646 A1 | 12/2005 | Lawson et al. |
| 2005/0275143 A1 | 12/2005 | Toth |
| 2006/0043651 A1 | 3/2006 | Yamamoto et al. |
| 2006/0051505 A1 | 3/2006 | Kortshagen et al. .......... 427/212 |
| 2006/0068989 A1 | 3/2006 | Ninomiya et al. |
| 2006/0094595 A1 | 5/2006 | Labarge |
| 2006/0096393 A1 | 5/2006 | Pesiri ........................ 73/863.21 |
| 2006/0105910 A1 | 5/2006 | Zhou et al. |
| 2006/0108332 A1 | 5/2006 | Belashchenko .......... 219/121.47 |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. ........ 422/151 |
| 2006/0166809 A1 | 7/2006 | Malek et al. |
| 2006/0211569 A1 | 9/2006 | Dang et al. |
| 2006/0213326 A1 | 9/2006 | Gollob et al. |
| 2006/0222780 A1 | 10/2006 | Gurevich et al. |
| 2006/0231525 A1 | 10/2006 | Asakawa et al. ................. 216/56 |
| 2007/0020167 A1 | 1/2007 | Han et al. |
| 2007/0044513 A1 | 3/2007 | Kear et al. |
| 2007/0048206 A1 | 3/2007 | Hung et al. |
| 2007/0049484 A1 | 3/2007 | Kear et al. |
| 2007/0063364 A1 | 3/2007 | Hsiao et al. ......................... 264/5 |
| 2007/0084308 A1 | 4/2007 | Nakamura et al. ............... 75/346 |
| 2007/0084834 A1 | 4/2007 | Hanus et al. ................ 219/121.5 |
| 2007/0087934 A1 | 4/2007 | Martens et al. .................. 52/214 |
| 2007/0092768 A1 | 4/2007 | Lee et al. |
| 2007/0153390 A1 | 7/2007 | Nakamura et al. |
| 2007/0161506 A1 | 7/2007 | Saito et al. |
| 2007/0163385 A1 | 7/2007 | Takahashi et al. |
| 2007/0172721 A1 | 7/2007 | Pak et al. |
| 2007/0178673 A1 | 8/2007 | Gole et al. |
| 2007/0221404 A1 | 9/2007 | Das et al. |
| 2007/0253874 A1 | 11/2007 | Foret |
| 2007/0266825 A1 | 11/2007 | Ripley et al. |
| 2007/0292321 A1 | 12/2007 | Plischke et al. |
| 2008/0006954 A1 | 1/2008 | Yubuta et al. |
| 2008/0026041 A1 | 1/2008 | Tepper et al. |
| 2008/0031806 A1 | 2/2008 | Gavenonis et al. |
| 2008/0038578 A1 | 2/2008 | Li |

(56) References Cited

U.S. PATENT DOCUMENTS

| | | |
|---|---|---|
| 2008/0045405 A1 | 2/2008 | Beutel et al. |
| 2008/0047261 A1 | 2/2008 | Han et al. |
| 2008/0056977 A1 | 3/2008 | Hung et al. |
| 2008/0057212 A1 | 3/2008 | Dorier et al. |
| 2008/0064769 A1 | 3/2008 | Sato et al. |
| 2008/0104735 A1 | 5/2008 | Howland |
| 2008/0105083 A1 | 5/2008 | Nakamura et al. |
| 2008/0116178 A1 | 5/2008 | Weidman |
| 2008/0125308 A1 | 5/2008 | Fujdala et al. |
| 2008/0125313 A1 | 5/2008 | Fujdala et al. |
| 2008/0138651 A1 | 6/2008 | Doi et al. |
| 2008/0175936 A1 | 7/2008 | Tokita et al. |
| 2008/0187714 A1 | 8/2008 | Wakamatsu et al. |
| 2008/0206562 A1 | 8/2008 | Stucky et al. |
| 2008/0207858 A1 | 8/2008 | Kowaleski et al. |
| 2008/0248704 A1 | 10/2008 | Mathis et al. |
| 2008/0274344 A1 | 11/2008 | Vieth et al. |
| 2008/0277092 A1 | 11/2008 | Layman et al. |
| 2008/0277266 A1 | 11/2008 | Layman |
| 2008/0277267 A1 | 11/2008 | Biberger et al. |
| 2008/0277268 A1 | 11/2008 | Layman |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |
| 2008/0280751 A1 | 11/2008 | Harutyunyan et al. |
| 2008/0280756 A1 | 11/2008 | Biberger |
| 2008/0283411 A1 | 11/2008 | Eastman et al. |
| 2008/0283498 A1 | 11/2008 | Yamazaki |
| 2008/0307960 A1 | 12/2008 | Hendrickson et al. |
| 2009/0010801 A1 | 1/2009 | Murphy et al. |
| 2009/0018008 A1 | 1/2009 | Jankowiak et al. |
| 2009/0054230 A1 | 2/2009 | Veeraraghavan et al. |
| 2009/0081092 A1 | 3/2009 | Yang et al. |
| 2009/0088585 A1 | 4/2009 | Schammel et al. |
| 2009/0092887 A1 | 4/2009 | McGrath et al. |
| 2009/0098402 A1 | 4/2009 | Kang et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0208367 A1 | 8/2009 | Calio et al. |
| 2009/0209408 A1 | 8/2009 | Kitamura et al. |
| 2009/0223410 A1 | 9/2009 | Jun et al. |
| 2009/0253037 A1 | 10/2009 | Park et al. |
| 2009/0274897 A1 | 11/2009 | Kaner et al. |
| 2009/0274903 A1 | 11/2009 | Addiego |
| 2009/0286899 A1 | 11/2009 | Hofmann et al. |
| 2009/0320449 A1 | 12/2009 | Beutel et al. |
| 2009/0324468 A1 | 12/2009 | Golden et al. |
| 2010/0050868 A1 | 3/2010 | Kuznicki et al. |
| 2010/0089002 A1 | 4/2010 | Merkel |
| 2010/0092358 A1 | 4/2010 | Koegel et al. |
| 2010/0124514 A1 | 5/2010 | Chelluri et al. |
| 2010/0166629 A1 | 7/2010 | Deeba |
| 2010/0180581 A1 | 7/2010 | Grubert et al. |
| 2010/0180582 A1 | 7/2010 | Mueller-Stach et al. |
| 2010/0186375 A1 | 7/2010 | Kazi et al. |
| 2010/0240525 A1 | 9/2010 | Golden et al. |
| 2010/0275781 A1 | 11/2010 | Tsangaris |
| 2010/0323118 A1 | 12/2010 | Mohanty et al. |
| 2011/0006463 A1 | 1/2011 | Layman |
| 2011/0030346 A1 | 2/2011 | Neubauer et al. |
| 2011/0049045 A1 | 3/2011 | Hurt et al. |
| 2011/0052467 A1 | 3/2011 | Chase et al. |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143926 A1 | 6/2011 | Yin et al. |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0152550 A1 | 6/2011 | Grey et al. |
| 2011/0158871 A1 | 6/2011 | Arnold et al. |
| 2011/0174604 A1 | 7/2011 | Duesel et al. |
| 2011/0243808 A1 | 10/2011 | Fossey et al. |
| 2011/0245073 A1 | 10/2011 | Oljaca et al. |
| 2011/0247336 A9 | 10/2011 | Farsad et al. |
| 2011/0305612 A1 | 12/2011 | Müller-Stach et al. |
| 2012/0023909 A1 | 2/2012 | Lambert et al. |
| 2012/0045373 A1 | 2/2012 | Biberger |
| 2012/0063963 A1 | 3/2012 | Watanabe et al. |
| 2012/0097033 A1 | 4/2012 | Arnold et al. |
| 2012/0122660 A1 | 5/2012 | Andersen et al. |
| 2012/0124974 A1 | 5/2012 | Li et al. |
| 2012/0171098 A1 | 7/2012 | Hung et al. |
| 2012/0214666 A1 | 8/2012 | van den Hoek et al. |
| 2012/0263633 A1 | 10/2012 | Koplin et al. |
| 2012/0308467 A1 | 12/2012 | Carpenter et al. |
| 2012/0313269 A1 | 12/2012 | Kear et al. |
| 2013/0034472 A1 | 2/2013 | Cantrell et al. |
| 2013/0079216 A1 | 3/2013 | Biberger et al. |
| 2013/0125970 A1 | 5/2013 | Ko et al. |
| 2013/0213018 A1 | 8/2013 | Yin et al. |
| 2013/0280528 A1 | 10/2013 | Biberger |
| 2013/0281288 A1 | 10/2013 | Biberger et al. |
| 2013/0294989 A1 | 11/2013 | Koch et al. |
| 2013/0316896 A1 | 11/2013 | Biberger |
| 2013/0331257 A1 | 12/2013 | Barcikowski et al. |
| 2013/0345047 A1 | 12/2013 | Biberger et al. |
| 2014/0018230 A1 | 1/2014 | Yin et al. |
| 2014/0120355 A1 | 5/2014 | Biberger |
| 2014/0128245 A1 | 5/2014 | Yin et al. |
| 2014/0140909 A1 | 5/2014 | Qi et al. |
| 2014/0148331 A1 | 5/2014 | Biberger et al. |
| 2014/0161693 A1 | 6/2014 | Brown et al. |
| 2014/0209451 A1 | 7/2014 | Biberger et al. |
| 2014/0228201 A1 | 8/2014 | Mendoza Gómez et al. |
| 2014/0243187 A1 | 8/2014 | Yin et al. |
| 2014/0249021 A1 | 9/2014 | van den Hoek et al. |
| 2014/0252270 A1 | 9/2014 | Lehman, Jr. |
| 2014/0263190 A1 | 9/2014 | Biberger et al. |
| 2014/0318318 A1 | 10/2014 | Layman et al. |
| 2014/0338519 A1 | 11/2014 | Biberger |
| 2015/0093312 A1 | 4/2015 | Yin et al. |

FOREIGN PATENT DOCUMENTS

| | | | |
|---|---|---|---|
| CN | 101301610 A | 11/2008 | |
| DE | 34 45 273 A1 | 6/1986 | |
| EP | 0 347 386 A1 | 12/1989 | |
| EP | 0 385 742 A1 | 9/1990 | |
| EP | 1 134 302 A1 | 9/2001 | |
| EP | 1 256 378 A2 | 11/2002 | |
| EP | 1 619 168 A1 | 1/2006 | |
| EP | 1 790 612 A1 | 5/2007 | |
| EP | 1 955 765 A1 | 8/2008 | |
| GB | 1 307 941 A | 2/1973 | |
| JP | 56-146804 | 11/1981 | ............ B22F 9/08 |
| JP | 61-086815 A | 5/1986 | |
| JP | 62-102827 A | 5/1987 | |
| JP | 63-214342 A | 9/1988 | |
| JP | 1-164795 A | 6/1989 | |
| JP | 2-6339 A | 1/1990 | |
| JP | 3-226509 A | 10/1991 | |
| JP | 5-193909 A | 8/1993 | |
| JP | 05-228361 A | 9/1993 | |
| JP | 05-324094 A | 12/1993 | |
| JP | 6-93309 A | 4/1994 | |
| JP | 6-135797 A | 5/1994 | |
| JP | 6-172820 A | 6/1994 | |
| JP | 6-272012 A | 9/1994 | |
| JP | H06-065772 | 9/1994 | |
| JP | 7031873 A | 2/1995 | |
| JP | 7-138020 A | 5/1995 | |
| JP | 7-207381 A | 8/1995 | |
| JP | 8-158033 A | 6/1996 | |
| JP | 8-217420 A | 8/1996 | |
| JP | 9-141087 A | 6/1997 | |
| JP | 10-130810 A | 5/1998 | |
| JP | 10-249198 A | 9/1998 | |
| JP | 11-502760 A | 3/1999 | |

(56) References Cited

FOREIGN PATENT DOCUMENTS

| | | |
|---|---|---|
| JP | 11-300198 A | 11/1999 |
| JP | 2000-220978 A | 8/2000 |
| JP | 2002-88486 A | 3/2002 |
| JP | 2002-241812 A | 8/2002 |
| JP | 2002-336688 A | 11/2002 |
| JP | 2003-126694 A | 5/2003 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |
| JP | 2006-87965 A | 4/2006 |
| JP | 2006-247446 A | 9/2006 |
| JP | 2006-260385 A | 9/2006 |
| JP | 2006-326554 A | 12/2006 |
| JP | 2007-29859 A | 2/2007 |
| JP | 2007-44585 A | 2/2007 |
| JP | 2007-46162 A | 2/2007 |
| JP | 2007-138287 A | 6/2007 |
| JP | 2007-203129 A | 8/2007 |
| SU | 493241 | 3/1976 |
| TW | 200611449 | 4/2006 |
| TW | 201023207 | 6/2010 |
| WO | WO-96/28577 A1 | 9/1996 |
| WO | WO-00/16882 | 3/2000 |
| WO | WO-00/72965 A1 | 12/2000 |
| WO | WO 02/092503 A1 | 11/2002 ............ C01B 21/064 |
| WO | WO-03/094195 A1 | 11/2003 |
| WO | 2004052778 A2 | 6/2004 |
| WO | WO-2005/063390 A1 | 7/2005 |
| WO | WO 2006/079213 A1 | 8/2006 ................. B01J 2/04 |
| WO | WO-2006/096205 A2 | 9/2006 |
| WO | WO-2007/144447 A1 | 12/2007 |
| WO | WO-2008/092478 A1 | 8/2008 |
| WO | WO-2008/130451 A2 | 10/2008 |
| WO | WO-2008/130451 A3 | 10/2008 |
| WO | WO-2009/017479 A1 | 2/2009 |
| WO | WO-2011/081833 A1 | 7/2011 |
| WO | WO-2012/028695 A2 | 3/2012 |
| WO | WO-2013/028575 A1 | 2/2013 |
| WO | WO-2013/093597 A2 | 6/2013 |
| WO | WO-2013/151557 A1 | 10/2013 |

OTHER PUBLICATIONS

Kenvin et al. "Supported Catalysts Prepared from Monuclear Copper Complexes: Catalytic Properties", Journal of Catalysis, pp. 81-91.
National Aeronautics and Space Administration, "Enthalpy", http://www.grc.nasa.gov/WWW/K-12/airplane/enthalpy.html, Nov. 23, 2009, 1 page.
Hanet al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.
United States Patent and Trademark Office, Office Action, mailed Feb. 18, 2010, U.S. Appl. No. 12/001,644, filed Dec. 11, 2007, First Named Inventor: Maximilian A. Biberger, 7 pages.
United States Patent and Trademark Office, Office Action, mailed Feb. 19, 2010, U.S. Appl. No. 12/152,109, filed May 9, 2008, First Named Inventor: Maximilian A. Biberger, 17 pages.
J. Heberlein, "New Approaches in Thermal Plasma Technology", Pure Appl. Chem., vol. 74, No. 3, 2002, pp. 327-335.
T. Yoshida, "The Future of Thermal Plasma Processing for Coating", Pure & Appl. Chem., vol. 66, No. 6, 1994 pp. 1223-1230.
A. Gutsch et al., "Gas-Phase Production of Nanoparticles", Kona No. 20, 2002, pp. 24-37.
Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I Ii, P. Fauchais, Universite de Limoges, 123 Avenue A. Thomas 87000, Limoges, F. , Pure & Chem, vol. 68, No. 5, pp. 1093-1099, 1996.
Van Oudenaren, Sarah A., United States Patent and Trademark Office, Office Action mailed Oct. 7, 2010, for U.S. Appl. No. 12/001,643, pp. 1-15.
Van Oudenaren, Sarah A., United States Patent and Trademark Office, Office Action mailed Oct. 4, 2010, for U.S. Appl. No. 12/474,081, pp. 1-16.
H. Konrad et al., "Nanostructured Cu—Bi Alloys Prepared by Co-Evaporation in a Continuous Gas Flow," NanoStructured Materials, vol. 7, No. 6, Apr. 1996, pp. 605-610.
M. Vardelle et al., "Experimental Investigation of Powder Vaporization in Thermal Plasma Jets," Plasma Chemistry and Plasma Processing, vol. 11, No. 2, Jun. 1991, pp. 185-201.
P. Fauchais et al., "Plasma Spray: Study of the Coating Generation," Ceramics International, Elsevier, Amsterdam, NL, vol. 22, No. 4, Jan. 1996, pp. 295-303.
P. Fauchais et al., "Les Dépôts Par Plasma Thermique," Revue Generale De L'Electricitie, RGE. Paris, FR, No. 2, Jan. 1993, pp. 7-12.
P. Fauchais et al, "La Projection Par Plasma: Une Revue," Annales De Physique, vol. 14, No. 3, Jun. 1989, pp. 261-310.
DERWENT English Abstract for publication No. SU 193241 A, Application No. 1973SU1943286 filed on Jul. 2, 1973, published on Mar. 1, 1976, entitled"Catalyst for Ammonia Synthesis Contains Oxides of Aluminium, Potassium, Calcium, Iron and Nickel Oxide for Increased Activity," 3 pgs.
Stiles, A. B. (Jan. 1, 1987). "Manufacture of Carbon-Supported Metal Catalysts," in Catalyst Supports and Supported Catalysts, Butterworth Publishers, MA, pp. 125-132.
Bateman, J. E. et al. (Dec. 17, 1998). "Alkylation of Porous Silicon by Direct Reaction with Alkenes and Alkynes," *Angew. Chem Int. Ed.* 37(19):2683-2685.
Carrot, G. et al. (Sep. 17, 2002). "Surface-Initiated Ring-Opening Polymerization: A Versatile Method for Nanoparticle Ordering," *Macromolecules* 35(22):8400-8404.
Chen, H.-S. et al. (Jul. 3, 2001). "On the Photoluminescence of Si Nanoparticles," *Mater. Phys. Mech.* 4:62-66.
Fojtik, A. et al. (Apr. 29, 1994). "Luminescent Colloidal Silicon Particles," *Chemical Physics Letters* 221:363-367.
Fojtik, A. (Jan. 13, 2006). "Surface Chemistry of Luminescent Colloidal Silicon Nanoparticles," *J. Phys. Chem. B*. 110(5):1994-1998.
Hua, F. et al. (Mar. 2006). "Organically Capped Silicon Nanoparticles With Blue Photoluminescence Prepared by Hydrosilylation Followed by Oxidation," *Langmuir* 22(9):4363-4370.
Jouet, R. J. et al. (Jan. 25, 2005). "Surface Passivation of Bare Aluminum Nanoparticles Using Perfluoroalkyl Carboxylic Acids," *Chem. Mater.*17(11):2987-2996.
Kim, N. Y. et al. (Mar. 5, 1997). "Thermal Derivatization of Porous Silicon with Alcohols," *J. Am. Chem. Soc.* 119(9):2297-2298.
Kwon, Y.-S. et al. (Apr. 30, 2003). "Passivation Process for Superfine Aluminum Powders Obtained by Electrical Explosion of Wires," *Applied Surface Science* 211:57-67.
Langner, A. et al. (Aug. 25, 2005). "Controlled Silicon Surface Functionalization by Alkene Hydrosilylation," *J. Am. Chem. Soc.* 127(37):12798-12799.
Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," *J. Am. Chem. Soc.* 127(7):6248-6256.
Li, X. et al. (May 25, 2004). "Surface Functionalization of Silicon Nanoparticles Produced by Laser-Driven Pyrolysis of Silane Followed by HF-HNO$_3$ Etching," *Langmuir* 20(11):4720-4727.
Liao, Y.-C. et al. (Jun. 27, 2006). "Self-Assembly of Organic Monolayers on Aerosolized Silicon Nanoparticles," *J.Am. Chem. Soc.* 128(28):9061-9065.
Liu, S.-M. et al. (Jan. 13, 2006). "Enhanced Photoluminescence from Si Nano-Organosols by Functionalization With Alkenes and Their Size Evolution," *Chem. Mater.* 18(3):637-642.

(56) References Cited

OTHER PUBLICATIONS

Neiner, D. (Aug. 5, 2006). "Low-Temperature Solution Route to Macroscopic Amounts of Hydrogen Terminated Silicon Nanoparticles," *J. Am. Chem. Soc.* 128:11016-11017.
Netzer, L. et al. (1983). "A New Approach to Construction of Artificial Monolayer Assemblies," *J. Am. Chem. Soc.* 105(3):674-676.
Sailor, M. J. (1997). "Surface Chemistry of Luminescent Silicon Nanocrystallites," *Adv. Mater.* 9(10):783-793.
Tao, Y.-T. (May 1993). "Structural Comparison of Self-Assembled Monolayers of *n*-Alkanoic Acids on the surfaces of Silver, Copper, and Aluminum," *J. Am. Chem. Soc.* 115(10):4350-4358.
Zou, J. et al. (Jun. 4, 2004). "Solution Synthesis of Ultrastable Luminescent Siloxane-Coated Silicon Nanoparticles," *Nano Letters* 4(7):1181-1186.
Non Final Office Action mailed on Nov. 16, 2011, for U.S. Appl. No. 12/152,096, filed May 9, 2008, for Biberger et al., 10 pages.
Final Office Action mailed on Jul. 11, 2012, for U.S. Appl. No. 12/152,096, filed May 9, 2008, for Biberger et al., 8 pages.
Ahmad, K. et al. (2008). "Hybrid Nanocomposites: A New Route Towards Tougher Alumina Ceramics," *Composites Science and Technology* 68: 1321-1327.
Babin, A. et al. (1985). "Solvents Used in the Arts," *Center for Safety in the Arts*: 16 pages.
Birlik, I. et al. (Jun. 15, 2010). "Nanoparticle Doped YBCO Films Prepared by Chemical Solution Deposition Method," *6th Nanoscience and Nanotechnology Conference*, Izmir, Turkey: 1 page.
Büchel, R. et al. (2009). "Influence of Pt Location on $BaCO_3$ or $Al_2O_3$ During $NO_x$ Storage Reduction," *Journal of Catalysis* 261: 201-207.
Chaim, R. et al. (2009). "Densification of Nanocrystalline $Y_2O_3$ Ceramic Powder by Spark Plasma Sintering," *Journal of European Ceramic Society* 29: 91-98.
Chau, J. K. H. et al. (2005). "Microwave Plasma Synthesis of Silver Nanopowders," *Materials Letters* 59: 905-908.
Chen, W.-J. et al. (Mar. 18, 2008). "Functional $Fe_3O_4/TiO_2$ Core/Shell Magnetic Nanoparticles as Photokilling Agents for Pathogenic Bacteria," *Small* 4(4): 485-491.
Cospheric LLC. (Mar. 13, 2010). "Porous Ceramics: Application for Polyethylene Microspheres," Microspheres Online, located at http://microspheres.us/microsphere-manufacturing/porous-ceramics-polyethylene-microspheres/177.html, last accessed Mar. 17, 2015, 6 pages.
Das, N. et al. (2001). "Influence of the Metal Function in the "One-Pot" Synthesis of 4-Methyl-2-Pentanone (Methyl Isobutyl Ketone) from Acetone Over Palladium Supported on Mg(Al)O Mixed Oxides Catalysts," *Catalysis Letters* 71(3-4): 181-185.
Date, A. R. et al. (1987). "The Potential of Fire Assay and Inductively Coupled Plasama Source Mass Spectrometry for the Determination of Platinum Group Elements in Geological Materials," *Analyst* 112: 1217-1222.
Faber, K. T. et al. (Sep. 1988). "Toughening by Stress-Induced Microcracking in Two-Phase Ceramics," *Journal of the American Ceramic Society* 71: C-399-C401.
Gangeri, M. et al. (2009). "Fe and Pt Carbon Nanotubes for the Electrocatalytic Conversion of Carbon Dioxide to Oxygenates," *Catalysis Today* 143: 57-63.
Ihlein, G. et al.(1998). "Ordered Porous Materials as Media for the Organization of Matter on the Nanoscale," *Applied Organometallic Chemistry* 12: 305-314.
Ji, Y. et al. (Nov. 2002) "Processing and Mechanical Properties of $Al_2O_3$-5 vol. % Cr Nanocomposites," *Journal of the European Ceramic Society* 22(12):1927-1936.
Lakis, R. E. et al. (1995). "Alumina-Supported Pt—Rh Catalysts: I. Microstructural Characterization," *Journal of Catalysis* 154: 261-275.
Lamouroux, E. et al. (2007). "Identification of Key Parameters for the Selective Growth of Single or Double Wall Carbon Nanotubes on $FeMo/Al_2O_3$ CVD Catalysts," *Applied Catalysts A: General* 323: 162-173.
Luo, J. et al. (2008). "Core/Shell Nanoparticles as Electrocatalysts for Fuel Cell Reactions," *Advanced Materials* 20: 4342-4347.
Martinez-Hansen, V. et al. (2009). "Development of Aligned Carbon Nanotubes Layers Over Stainless Steel Mesh Monoliths," *Catalysis Today* 1475: S71-S75.
Mignard, D. et al. (2003). "Methanol Synthesis from Flue-Gas $CO_2$ and Renewable Electricity: A Feasibility Study," *International Journal of Hydrogen Energy* 28: 455-464.
Panchula, M. L. et al. (2003). "Nanocrystalline Aluminum Nitride: I, Vapor-Phase Synthesis in a Forced-Flow Reactor," *Journal of the American Ceramic Society* 86(7): 1114-1120.
Park, H.-Y. et al. (May 30, 2007). "Fabrication of Magnetic Core@Shell Fe Oxide@Au Nanoparticles for Interfacial Bioactivity and Bio-Separation," *Langmuir* 23: 9050-9056.
Park, N.-G. et al. (Feb. 17, 2004). "Morphological and Photoelectrochemical Characterization of Core-Shell Nanoparticle Films for Dye-Sensitized Solar Cells: Zn—O Type Shell on $SnO_2$ and $TiO_2$ Cores," *Langmuir* 20: 4246-4253.
"Plasma Spray and Wire Flame Spray Product Group," located at http://www.processmaterials.com/spray.html, published by Process Materials, Inc., last accessed Aug. 5, 2013, 2 pages.
"Platinum Group Metals: Annual Review 1996" (Oct. 1997). *Engineering and Mining Journal*, p. 63.
Rahaman, R. A. et al. (1995). "Synthesis of Powders," in *Ceramic Processing and Sintering*. Marcel Decker, Inc., New York, pp. 71-77.
Schimpf, S. et al. (2002). "Supported Gold Nanoparticles: In-Depth Catalyst Characterization and Application in Hydrogenation and Oxidation Reactions," *Catalysis Today* 2592: 1-16.
Strobel, R. et al. (2003). "Flame-made Platinum/Alumina: Structural Properties and Catalytic Behaviour in Enantioselective Hydrogenation," *Journal of Catalysis* 213: 296-304.
Subramanian, S. et al. (1991). "Structure and Activity of Composite Oxide Supported Platinum—Iridium Catalysts," *Applied Catalysts* 74: 65-81.
Ünal, N. et al. (Nov. 2011). "Influence of WC Particles on the Microstructural and Mechanical Properties of 3 mol% $Y_2O_3$ Stabilized $ZrO_2$ Matrix Composites Produced by Hot Pressing,"*Journal of the European Ceramic Society* (31)13: 2267-2275.
Viswanathan, V. et al. (2006). "Challenges and Advances in Nanocomposite Processing Techniques," *Materials Science and Engineering R* 54: 121-285.
Wan, J. et al. (2005). "Spark Plasma Sintering of Silicon Nitride/Silicon Carbide Nanocomposites with Reduced Additive Amounts," *Scripta Materialia* 53: 663-667.
U.S. Appl. No. 12/152,084, filed May 9, 2008, for Biberger.
U.S. Appl. No. 12/152,111, filed May 9, 2008, for Biberger et al.
U.S. Appl. No. 12/954,813, filed Nov. 26, 2010, for Biberger.
U.S. Appl. No. 12/954,822, filed Nov. 26, 2010, for Biberger.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,239, filed Dec. 14, 2010, for Biberger.
U.S. Appl. No. 12/969,128, filed Dec. 15, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,457, filed Nov. 15, 2010, for Leamon et al.
U.S. Appl. No. 13/028,693, filed Feb. 16, 2011, for Biberger.
U.S. Appl. No. 13/291,983, filed Nov. 8, 2011, for Layman et al.

\* cited by examiner

HIGHLY TURBULENT QUENCH CHAMBER

CROSS-REFERENCE TO RELATED APPLICATIONS

The present application claims priority to U.S. Provisional Application Serial Number 60/928,946, filed May 11, 2007, entitled "MATERIAL PRODUCTION SYSTEM AND METHOD," which is hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE INVENTION

Gas or vapor phase particle production is an important technique for producing engineered materials. The present invention relates to methods of and an apparatus for quenching a reactive medium containing gas or vapor phase particles.

BACKGROUND OF THE INVENTION

In a particle producing reactor, basic product species are formed within extremely short time spans following ejection of a hot, reactive medium from an energy delivery zone. Following ejection, further formation mechanisms determine the ultimate characteristics of the final product.

Although chemical reactions such as nucleation and surface growth within precursor materials occur largely during energy delivery, these formation mechanisms continue to be active in the first short moments following ejection. More prevalent in the post-ejection time period are bulk formation mechanisms such as coagulation and coalescence, which operate on already formed particles. Any proper conditioning of the hot, reactive medium following ejection from the energy delivery zone must account for these and other formation mechanisms to form a final product having desired characteristics. In some instances, maintaining a reactive mixture at too high a temperature can lead to overly agglomerated particles in the final product.

In addition to particle formation, proper conditioning must account for post-formation processing of the product. Although particles, once formed, cool rapidly through radiative heat loss, the residual gas in which they are entrained after formation cools much more slowly, and especially so when confined. Confinement is necessary to some degree in any controlled-environment processing system—and economic concerns usually dictate relatively small, confining controlled environments. Therefore, such systems must provide efficient mechanisms for cooling of the entire gas-particle product, yet also provide for efficient transport of the product to collection points within the system.

Transport of particles within a gas stream relies on entrainment of the particle, which is largely a function of particle properties, e.g. mass, temperature, density, and inter-particle reactivity, as well as gas properties, e.g., density, velocity, temperature, density, viscosity, and composite properties, such as particle-gas reactivity. Cooling of a gas, by definition, affects gas temperature, but also may easily lead to changes in other properties listed above, exclusive of mass. In view of the foregoing, balancing efficient cooling and transportation of a gas-particle product requires careful optimization of process parameters, which the present invention seeks to achieve.

SUMMARY OF THE INVENTION

In one aspect of the present invention, a quench chamber is disclosed. The quench chamber comprises a frusto-conical body having a wide end, a narrow end, and a quench region formed between the wide end and the narrow end. The quench chamber also includes a reactive mixture inlet configured to receive a reactive mixture and to supply the reactive mixture into the quench region in the direction of the narrow end. The quench chamber further comprises a conditioning fluid inlet configured to supply a conditioning fluid into the quench region in the direction of the narrow end. The frusto-conical body is configured to produce a turbulent flow within the quench region with the supply of the conditioning fluid into the quench region, thereby promoting the quenching of the reactive mixture with the conditioning fluid to form a cooled gas-particle mixture. A gas-particle mixture outlet is disposed at the narrow end. The outlet is configured to receive the cooled gas-particle mixture from the quench region.

In another aspect of the present invention, an apparatus for cooling a reactive mixture to condense particle therefrom is disclosed. The apparatus comprises a plasma reactor configured to form the reactive mixture from plasma and a precursor material. The apparatus also includes a quench chamber comprising a frusto-conical body having a wide end, a narrow end, and a quench region formed between the wide end and the narrow end. The quench chamber is configured to receive the reactive mixture from the plasma reactor through a reactive mixture inlet into the quench region, to receive a conditioning fluid from a conditioning fluid supply through at least one fluid supply inlet, and to flow the conditioning fluid into the quench region. The frusto-conical body is configured to produce a turbulent flow within the quench region with the flow of the conditioning fluid into the quench region, thereby promoting the quenching of the reactive mixture with the conditioning fluid to form a cooled gas-particle mixture. A suction generator is fluidly coupled to an outlet at the narrow end of the quench region and configured to generate suction at the narrow end to force the cooled gas-particle mixture out of the quench chamber through the outlet.

In yet another aspect of the present invention, a method of cooling a reactive mixture in a quench chamber is disclosed. The method comprises flowing the reactive mixture from a reactor through a reactive mixture inlet into a quench region having a frusto-conical shape with a wide end and a narrow end. The quench region is formed within a portion of a quench chamber having a frusto-conical surface, wherein the flow of the reactive mixture forms a mixture momentum vector leading from the wide end to the narrow end. A conditioning fluid flows into the quench region through at least one fluid supply inlet along a plurality of conditioning momentum vectors from the wide end to the narrow end. This flow of conditioning fluid into the quench region forms a turbulent flow within the quench region. The conditioning fluid and the reactive mixture are mixed within the turbulent flow of the quench region, thereby quenching the reactive mixture with the conditioning fluid to form a cooled gas-particle mixture. The cooled gas-particle mixture is flown out of an outlet at the narrow end of the quench region. This cooled gas-particle mixture comprises a plurality of particles entrained in a fluid.

In a preferred embodiment, the supply of conditioning fluid into the quench region is configured to produce a flow having a Reynolds Number of at least 1000.

In one embodiment, the frusto-conical body is configured to supply the conditioning fluid to the quench region along a plurality of momentum vectors, and at least two of the plurality of momentum vectors form an angle between them that is greater than or equal to 90 degrees.

In another embodiment, the reactive mixture inlet is configured to supply the reactive mixture into the quench region along a first momentum vector, the frusto-conical body is configured to supply the conditioning fluid to the quench region along a second momentum vector, and the second momentum vector has an oblique angle greater than 20 degrees relative to the first momentum vector.

Furthermore, the gas-particle mixture outlet can be positioned a first distance away from the center of the reactive mixture inlet, and the frusto-conical body can be positioned at least a second distance away from the perimeter of the reactive mixture inlet, forming a gap therebetween. Preferably, the first distance is greater than the second distance. The relative positioning of the frusto-conical body and the reactive mixture inlet can be adjustable, whereby the first distance and the second distance are adjustable.

Other components and aspects of the present invention can be configured to be adjustable as well. For example, the volume of the quench region can be adjustable.

Additionally, the frusto-conical body is preferably configured to supply the conditioning fluid to the quench region along a plurality of momentum vectors. The angle at which the frusto-conical body supplies the conditioning fluid to the quench region can be adjustable.

Furthermore, a cooling system can be coupled to the frusto-conical body, wherein the cooling system is configured to control a temperature of the frusto-conical body. A fluid supply element can also be provided, wherein the fluid supply element is configured to adjust the flow rate of the conditioning fluid into the quench region.

DETAILED DESCRIPTION OF THE INVENTION

The description below concerns several embodiments of the invention. The discussion references the illustrated preferred embodiment. However, the scope of the present invention is not limited to either the illustrated embodiment, nor is it limited to those discussed, to the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders(nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

Figure 1:
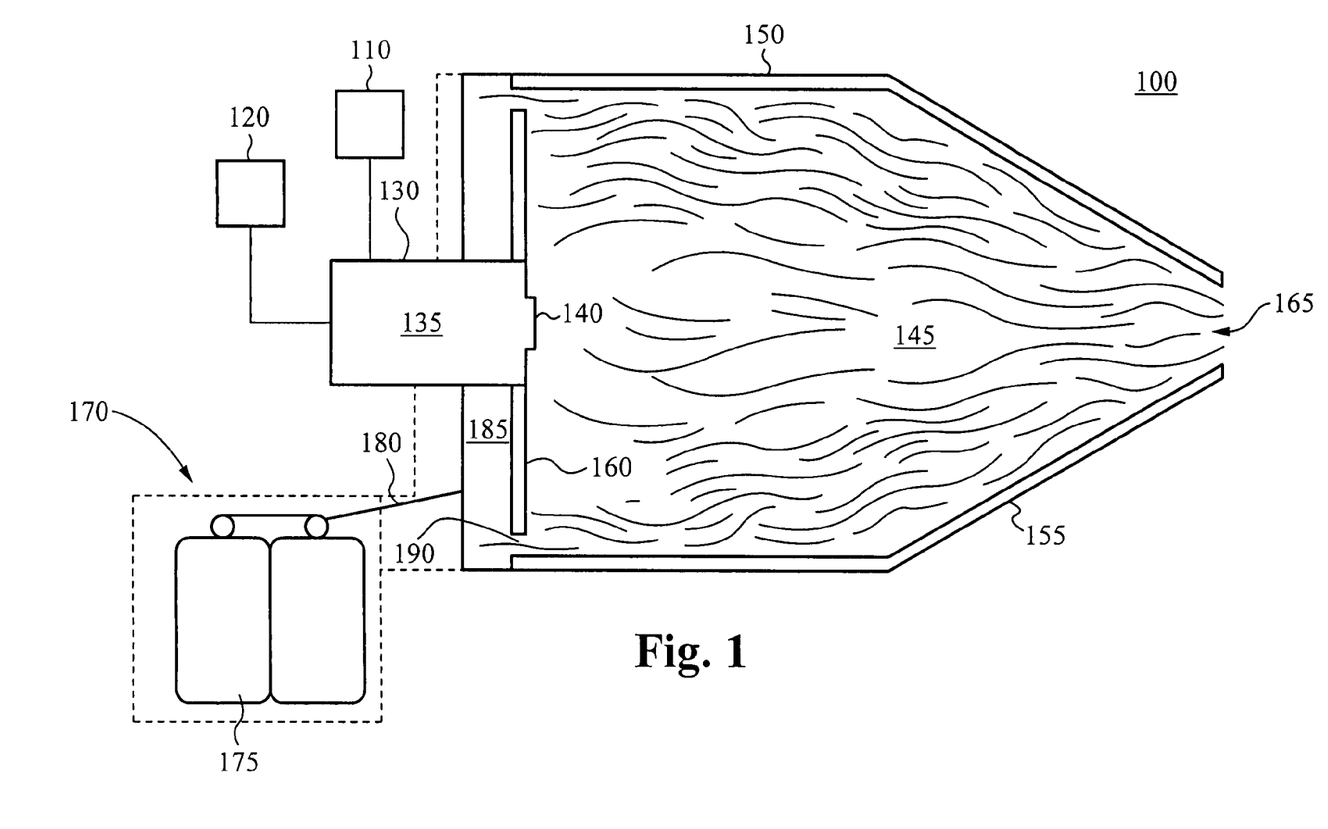
FIG. 1 is a cross-sectional view of one embodiment of a particle production system in accordance with the principles of the present invention.

Referring now to FIG. 1, a gas phase particle production system 100 is presented. The system 100 comprises a precursor supply device 110 and a working gas supply device 120 both fluidly coupled to a plasma production chamber 130 having an energy delivery zone 135 formed therein. The plasma production chamber 130 is fluidly coupled with an injection port 140 of a constricting quench chamber 145, thereby allowing the energy delivery zone 135 to fluidly communicate with the quench chamber 145. One or more ports 190 also allow fluid communication of the quench chamber 145 with a controlled atmosphere system 170 (indicated by the dotted lines). The quench chamber 145 is also fluidly coupled with an ejection port 165.

Generally, the plasma production chamber 130 operates as a reactor, producing an output comprising particles within a gas stream. Particle production includes the steps of combination, reaction, and conditioning. In an exemplary embodiment, the present invention uses a nano-powder production system similar to those disclosed in U.S. patent application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such a nano-powder production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas. As it moves, the mixture cools and particles are formed therein. The still-energetic output mixture, comprising hot gas and energetic particles, is emitted from the plasma reactor.

In an exemplary embodiment, the plasma production chamber 130 combines precursor material (preferably in powder form) supplied from the precursor supply device 110 and working gas supplied from the working gas supply device 120 within the energy delivery zone 135, where the working gas is energized to form a plasma. The plasma is applied to the precursor material within the energy delivery zone 135 to form an energized, reactive mixture. This mixture comprises one or more materials in at least one of a plurality of phases, which may include vapor, gas, and plasma.

The reactive mixture flows from the energy delivery zone 135 into the constricting quench chamber 145 through the injection port 140. As the hot mixture moves from the energy delivery zone 135, it expands rapidly within the quench chamber 145 and cools. While the mixture flows into the quench chamber 145, the ports 190 supply conditioning fluid along the inner surfaces of the quench chamber 145. The conditioning fluid combines, at least to some extent, with the mixture, and flows from the quench chamber 145 through the ejection port 165.

During a period immediately after entering the quench chamber 145, particle formation occurs. Furthermore, the supply of conditioning fluid along the inner surfaces of the quench chamber 145 works to condition the reactive mixture, to maintain entrainment of the particles therein, and to prevent the depositing of material on the inner surfaces of the quench chamber 145.

Still referring to FIG. 1, the structure of the quench chamber 145 can be formed of relatively thin walled components capable of dissipating substantial heat. For example, the thin-walled components can conduct heat from inside the chamber and radiate the heat to the ambient. The quench chamber 145 comprises a substantially cylindrical surface 150, a cone-like (frusto-conical) surface 155, and an annular surface 160 connecting the injection port 140 with the cylindrical surface 150. The cylindrical surface 150, having a large diameter relative to the size of the injection port 140, provides accommodation for the expansion of the reactive mixture that occurs after the mixture flows into the quench chamber 145. The cone-like surface 155 extends from the cylindrical surface 150, away from the injection port 140 and towards the ejection port 165. The cone-like surface 155 is sufficiently smoothly varying so as to not unduly compress fluid flowing from through the quench chamber 145 to the ejection port 165.

Substantial heat is emitted, mostly in the form of radiation, from the mixture following its entry into the quench chamber 145. The quench chamber 145 is preferably designed to dissipate this heat efficiently. For example, the surfaces of the quench chamber 145 are preferably exposed to a cooling apparatus (not shown).

Still referring to FIG. 1, the controlled atmosphere system 170 preferably comprises a chamber 185 into which conditioning fluid is introduced from a reservoir 175 through a conduit 180. The conditioning fluid preferably comprises argon. However, other inert, relatively heavy gases are equally preferred. Furthermore, the preferable mechanism of providing the conditioning fluid into the quench chamber 145 is the formation of a pressure differential between the quench chamber 145 and the outlet 165. Such pressure differential will draw the conditioning fluid into the quench chamber 145 through the ports 190. Other less preferred methods of providing the conditioning fluid include, but are not limited to, forming positive pressure within the chamber 185.

The frusto-conical shape of the quench chamber 145 can provide a modest amount of turbulence within the quench region, thereby promoting the mixing of the conditioning fluid with the reactive mixture, and increasing the quenching rate beyond prior art systems. However, in some situations, an even greater increase in quenching rate may be desired. Such an increase in quenching rate can be achieved by creating a highly turbulent flow within a region of a quench chamber where the conditioning fluid is mixed with the reactive mixture.

Figure 2:
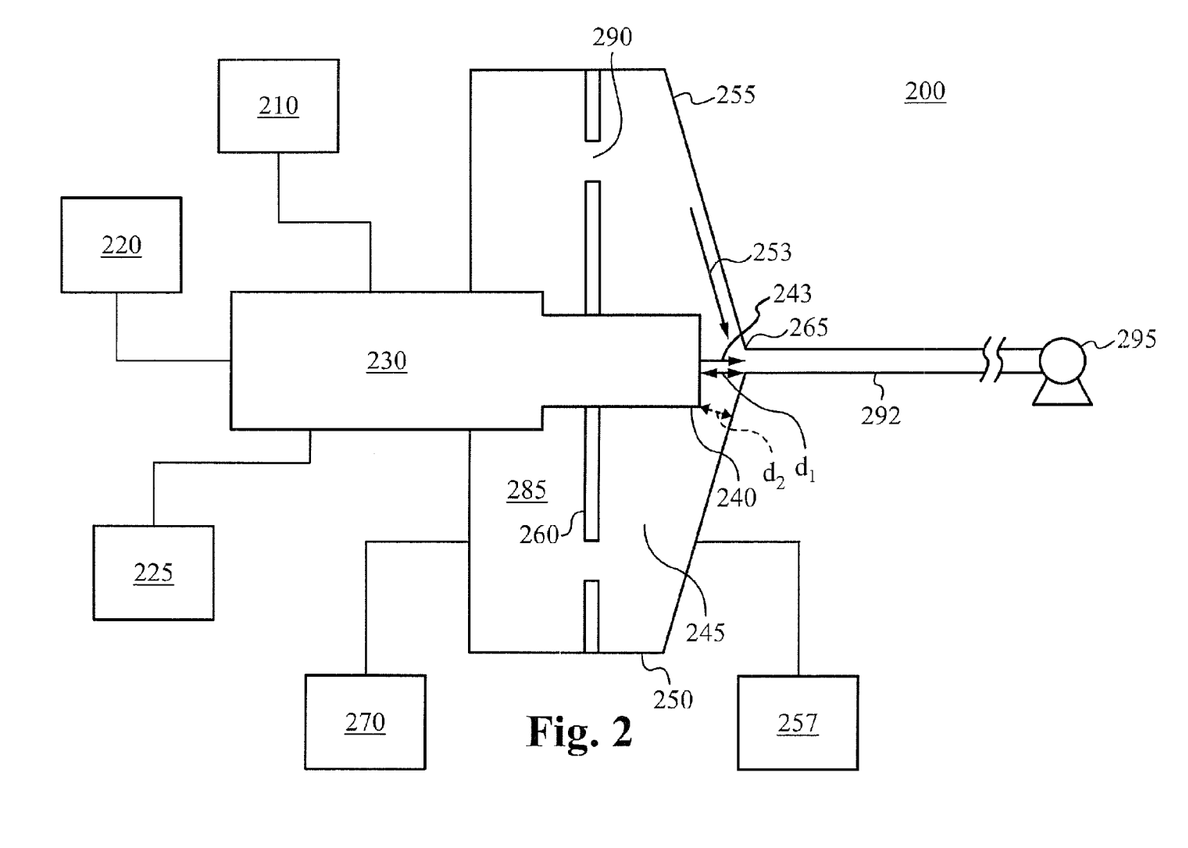
FIG. 2 is a cross-sectional view of one embodiment of a particle production system with a highly turbulent quench chamber in accordance with the principles of the present invention.

FIG. 2 illustrates a gas phase particle production system 200 with a highly turbulent quench chamber 245. The system 200 comprises a precursor supply device 210 a working gas supply device 220 fluidly coupled to a plasma production and reaction chamber 230, similar to plasma production chamber 130 discussed above with reference to FIG. 1. An energy delivery system 225 is also coupled with the plasma production and reactor chamber 230. The plasma production and reactor chamber 230 includes an injection port 240 that communicates fluidly with the constricting quench chamber 245. One or more ports 290 can also allow fluid communication between the quench chamber 245 and a controlled atmosphere system 270, similar to controlled atmosphere system 170 in FIG. 1. The quench chamber 245 is also fluidly coupled to an outlet 265.

Generally, the chamber 230 operates as a reactor, similar to chamber 130 in FIG. 1, producing an output comprising particles within a gas stream. Production includes the basic steps of combination, reaction, and conditioning as described later herein. The system combines precursor material supplied from the precursor supply device 210 and working gas supplied from the working gas supply device 220 within the energy delivery zone of the chamber 230. The system energizes the working gas in the chamber 230 using energy from the energy supply system 290, thereby forming a plasma. The plasma is applied to the precursor material within the chamber 230 to form an energized, reactive mixture. This mixture comprises one or more materials in at least one of a plurality of phases, which may include vapor, gas, and plasma. The reactive mixture flows from the plasma production and reactor chamber 230 into the quench chamber 245 through an injection port 240.

The quench chamber 245 preferably comprises a substantially cylindrical surface 250, a frusto-conical surface 255, and an annular surface 260 connecting the injection port 240 with the cylindrical surface 250. The frusto-conical surface 260 narrows to meet the outlet 265. The plasma production and reactor chamber 230 includes an extended portion at the end of which the injection port 240 is disposed. This extended portion shortens the distance between the injection port 240 and the outlet 265, reducing the volume of region in which the reactive mixture and the conditioning fluid will mix, referred to as the quench region. In a preferred embodiment, the injection port 240 is arranged coaxially with the outlet 265. The center of the injection port is positioned a first distance $d_1$ from the outlet 265. The perimeter of the injection port is positioned a second distance $d_2$ from a portion of the frusto-conical surface 255. The injection port 240 and the frusto-conical surface 255 form the aforementioned quench region therebetween. The space between the perimeter of the injection port 240 and the frusto-conical surface 255 forms a gap therebetween that acts as a channel for supplying conditioning fluid into the quench region. The frusto-conical surface 255 acts as a funneling surface, channeling fluid through the gap and into the quench region.

While the reactive mixture flows into the quench chamber 245 along a momentum vector 243, the ports 290 supply conditioning fluid into the quench chamber 245. The conditioning fluid then moves along the frusto-conical surface 255, through the gap between the injection port 240 and the frusto-conical surface 255, and into the quench region along momentum vectors, such as momentum vector 253. In some embodiments, the controlled atmosphere system 270 is configured to control the volume flow rate or mass flow rate of the conditioning fluid supplied to the quench region.

As the reactive mixture moves out of the injection port 240, it expands and mixes with the conditioning fluid. Preferably, the angle at which the conditioning fluid is supplied produces a high degree of turbulence and promotes mixing with the reactive mixture. This turbulence can depend on many parameters. In a preferred embodiment, one or more of these parameters is adjustable to control the level of turbulence. These factors include the flow rates of the conditioning fluid, the temperature of the frusto-conical surface 255, the angle of the frusto-conical surface 255 (which affects the angle at which the conditioning fluid is supplied into the quench region), and the size of the quench region. For example, the relative positioning of the frusto-conical surface 255 and the injection port 240 is adjustable, which can be used to adjust the volume of quench region. These adjustments can be made in a variety of different ways, using a variety of different mechanisms, including, but not limited to, automated means and manual means.

During a brief period immediately after entering the quench chamber 245, particle formation occurs. The degree to which the particles agglomerate depends on the rate of cooling. The cooling rate depends on the turbulence of the flow within the quench region. Preferably, the system is adjusted to form a highly turbulent flow, and to form very dispersed particles. For example, in preferred embodiments, the turbidity of the flow within the quench region is such that the flow has a Reynolds Number of at least 1000.

Still referring to FIG. 2, the structure of the quench chamber 245 is preferably formed of relatively thin walled components capable of dissipating substantial quantities of heat. For example, the thin-walled components can conduct heat from inside the chamber and radiate the heat to the ambient.

Substantial heat is emitted, mostly in the form of radiation, from the reactive mixture following its entry into the quench chamber 245. The quench chamber 245 is designed to dissipate this heat efficiently. The surfaces of the quench chamber 245 are preferably exposed to a cooling system 257. In a preferred embodiment, the cooling system is configured to control a temperature of the frusto-conical surface 255.

Following injection into the quench region, cooling, and particle formation, the mixture flows from the quench chamber 245 through the outlet port 265. Suction generated by a generator 295 moves the mixture and conditioning fluid from the quench region into the conduit 292. From the outlet port 265, the mixture flows along the conduit 292, toward the suction generator 295. Preferably, the particles are removed from the mixture by a collection or sampling system (not shown) prior to encountering the suction generator 295.

Still referring to FIG. 2, the controlled atmosphere system 270 comprises a chamber 285, fluidly coupled to the quench region through port(s) 290, into which conditioning fluid is introduced from a reservoir, such as reservoir 175, through a conduit 280. As described above, the conditioning fluid preferably comprises argon. However, other inert, relatively heavy gases are equally preferred. Also, as discussed above, the preferable mechanism of providing the conditioning fluid into the quench chamber 245 is the formation of a pressure differential between the quench chamber 245 and the outlet 265. Such pressure differential will draw the conditioning fluid into the quench chamber 245 through the ports 290. Other methods of providing the conditioning fluid include, but are not limited to, forming positive pressure within the chamber 285.

Figure 3A:
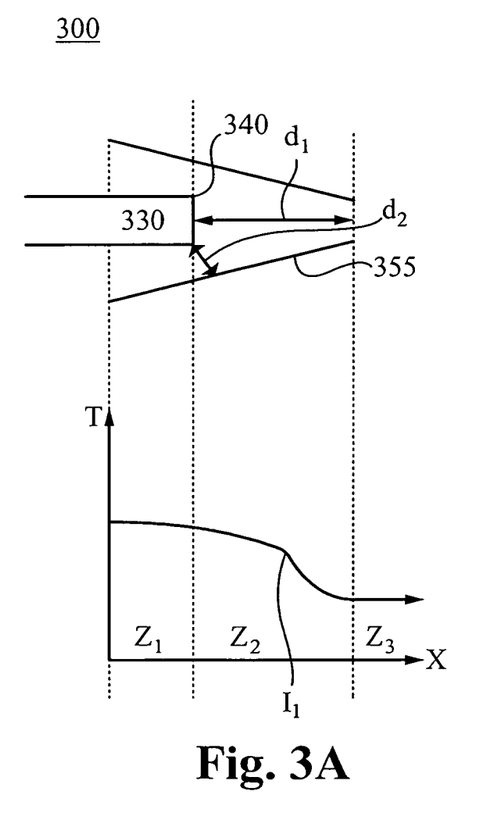
FIG. 3A is a combined schematic cross-sectional view of a portion of a particle production system and a corresponding graph of quench rate in accordance with the principles of the present invention.
Figure 3B:
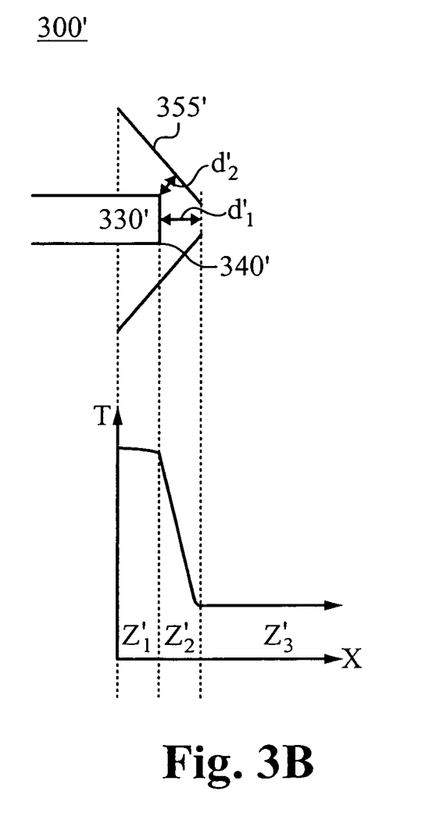
FIG. 3B is a combined schematic cross-sectional view of a portion of a particle production system with a highly turbulent quench chamber and a corresponding graph of quench rate in accordance with the principles of the present invention.
Figure 4A:
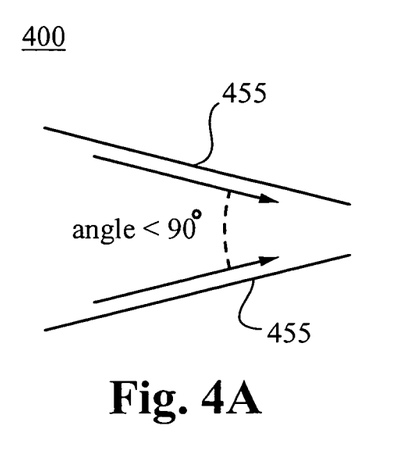
FIG. 4A is a cross-sectional view of one embodiment of conditioning fluid momentum vectors within a quench region of a quench chamber in accordance with the principles of the present invention.
Figure 4B:
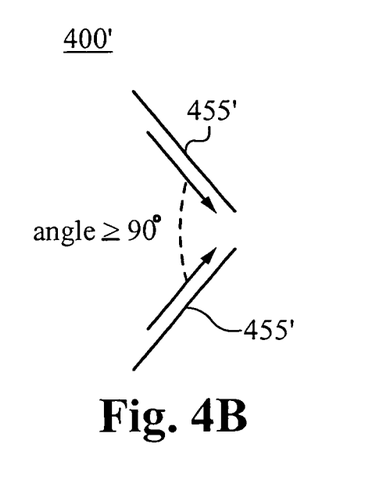
FIG. 4B is a cross-sectional view of one embodiment of conditioning fluid momentum vectors within a highly turbulent quench region of a quench chamber in accordance with the principles of the present invention.
Figure 5:
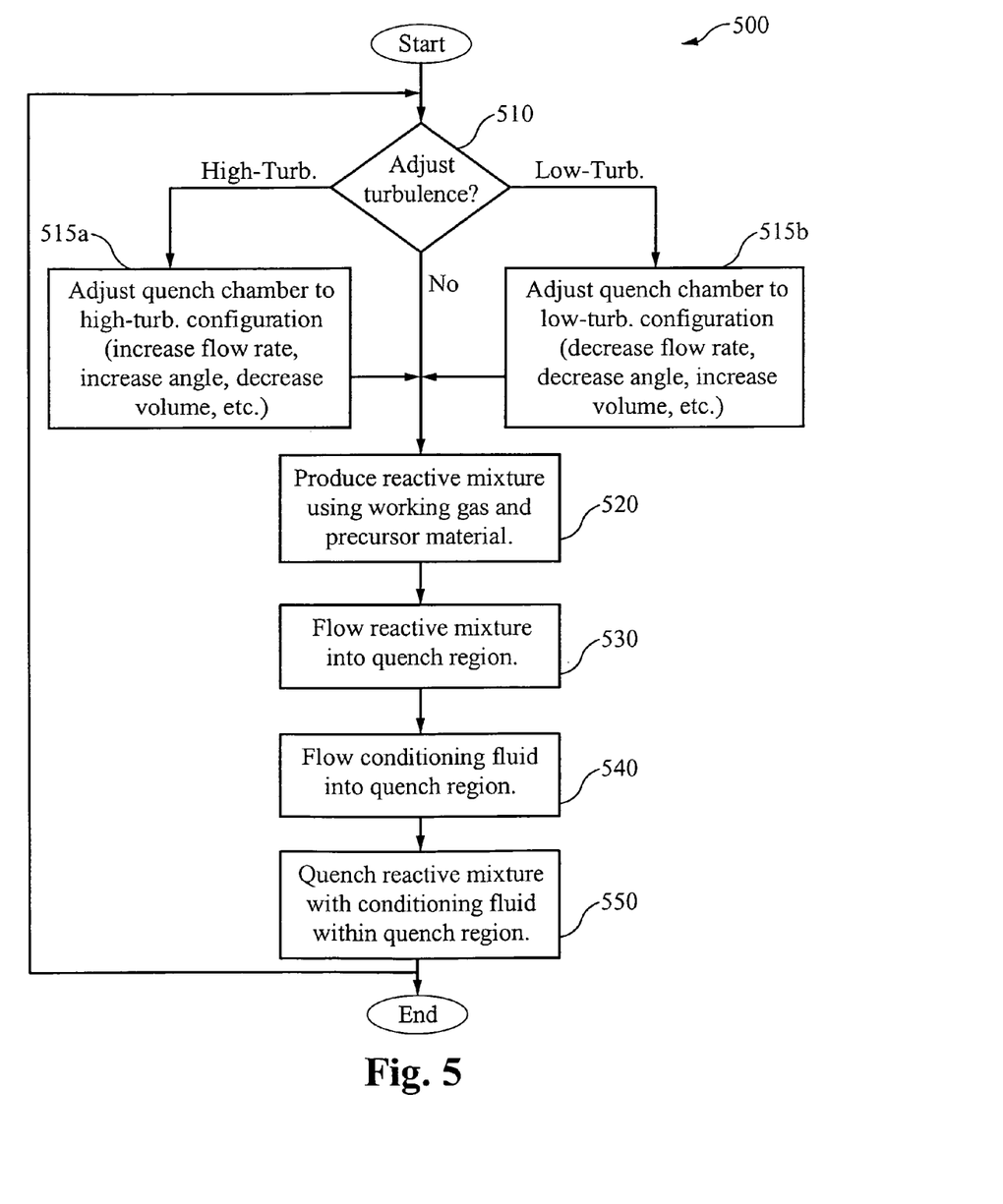
FIG. 5 is a flowchart illustrating one embodiment of a method of quenching a reactive mixture to condense and form particles therefrom in accordance with the principles of the present invention.

FIGS. 3A and 3B illustrate the effect of adjustments made within embodiments of the present invention on quench rates in particle production systems. FIG. 3A illustrates a portion of a low turbulence system 300. The reactive mixture flows from the reactor 330 through the injection port 340, and into the quench region formed between the injection port 340 and the frusto-conical surface 355. The mixture flows toward a narrow end of the frusto-conical surface 355. The quench region is described by the parameters $d_1$, the distance between the center of the injection port 340 and the narrow end of the quench region, and $d_2$, the distance between the perimeter of the injection port 340 and the frusto-conical surface 355.

The graph portion of FIG. 3A charts exemplary variations of the mixture temperature as it travels from the reactor 330, through the injection port 340, into the quench region, and towards the narrow end of the quench region. Within the reactor 330, the region $Z_1$, the temperature remains substantially constant. Once ejected, the mixture enters the quench region, $Z_2$, where it expands and initially cools rapidly. During this initial cooling, particles begin to form.

However, at the inflection point $I_1$, the forces tending to expand the mixture and inertial forces of the low turbulence gas begin to equilibrate. At this point, little mixing takes place between the hot mixture and the conditioning fluid. The temperature of the mixture continues to decrease, but does so at a much lower rate. During this time, the temperature remains high enough that the particles can agglomerate together to form large masses of particles.

Eventually, as these particles and the hot gas they are mixed with become entrained in the conditioning fluid and move out of the narrow end into the conduit region, $Z_3$, temperatures become low enough that no further agglomeration takes place.

FIG. 3B illustrates a portion of a high turbulence system 300'. The reactive mixture flows from the reactor 330' through the injection port 340', and into the quench region formed between the injection port 340' and the frusto-conical surface 355'. The mixture flows toward a narrow end of the frusto-conical surface 355'. The quench region is described by the parameters $d'_1$, the distance between the center of the injection port 340' and the narrow end of the quench region, and $d'_2$, the distance between the perimeter of the injection port 340' and the frusto-conical surface 355'.

The graph portion of FIG. 3B charts exemplary variations of the mixture temperature as it travels from the reactor 330', through the injection port 340', into the quench region, and towards the narrow end of the quench region. Within the reactor 330', the region $Z'_1$, the temperature remains substantially constant. Once ejected, the mixture enters the quench region, $Z'_2$, where it expands slightly and cools rapidly. The high turbulence flow within the quench region continues to mix conditioning fluid with the reactive mixture through the $Z'_2$ region and cools the mixture smoothly and rapidly until the conditioning fluid and reactive mixture reach thermal equilibrium. During this cooling, particles form. Because the mixture is cooled more rapidly in the system of 3B than in 3A, there is a shorter time period during which agglomeration can occur.

As the mixture of particles and hot gas continues to mix with the conditioning fluid, the mixture of gas and particles flows out of the narrow end into the conduit region, $Z'_3$. Overall, the quench period within a high turbulence quench region, as in some embodiments of the present invention, is much shorter than in a low turbulence quench region.

Therefore, the high turbulence produced by the embodiments of the present invention decreases the period during which particles formed can agglomerate with one another, thereby producing particles of more uniform size, and in some instances, producing smaller-sized particles. Both of these features lead to particles with increased dispersibility and increased ratio of surface area to volume.

As discussed above, the angle of the frusto-conical surface affects the angle at which the conditioning fluid is supplied into the quench region, which can affect the level of turbulence in the quench region. The conditioning fluid preferably flows into the quench region along a plurality of momentum vectors. The greater the degree of the angle between the momentum vectors, the higher the level of turbulence that will be produced. In a preferred embodiment, the high turbulent quench chamber comprises a frusto-conical surface that is configured to funnel at least two conditioning fluid momentum vectors into the quench region such that there is at least a 90 degree angle between the two momentum vectors.

FIG. 4A is a cross-sectional view of one embodiment 400 of conditioning fluid momentum vectors within a quench region of a low-turbulence quench chamber, such as the quench chamber illustrated in FIG. 1 or FIG. 3A. In FIG. 4A, the conditioning fluid flows into the quench region along momentum vectors represented by the arrows. As can be seen, the angle of the momentum vectors corresponds to the angle of the frusto-conical surface 455. In FIG. 4A, the angle formed between the momentum vectors is less than 90 degrees.

FIG. 4B is a cross-sectional view of one embodiment 400' of conditioning fluid momentum vectors within a quench region of a high-turbulence quench chamber, such as the quench chamber illustrated in FIG. 2 or FIG. 3B. In FIG. 4B, the conditioning fluid flows into the quench region along momentum vectors represented by the arrows. As can be seen, the angle of the momentum vectors corresponds to the angle of the frusto-conical surface 455'. In FIG. 4A, the angle formed between the momentum vectors is greater than or equal to 90 degrees.

It is contemplated that other angle degree thresholds may be applied as well. For example, attention may also be paid to the angle formed between at least one of the conditioning fluid momentum vectors and the momentum vector of the reactive mixture. In one embodiment of a highly turbulent quench chamber, a reactive mixture inlet is configured to supply the reactive mixture into the quench region along a first momentum vector, the frusto-conical surface is configured to supply the conditioning fluid to the quench region along a second momentum vector, and the second momentum vector has an oblique angle greater than 20 degrees relative to the first momentum vector.

FIG. 5 is a flowchart illustrating one embodiment of a method 500 of quenching a reactive mixture to condense and form particles therefrom in accordance with the principles of the present invention. At step 510, it is determined whether or not (and how) the turbulence in the quench region should be adjusted.

If it is determined that adjustments should be made to increase the turbulence to a higher turbulence, then the process continues on to step 315*a* where such adjustments are made to the quench chamber in the direction of a high-turbulence configuration. Such adjustments can include, but are not limited to, increasing the flow rate of the conditioning fluid, increasing the angle of the frusto-conical surface (thus increasing the angle between the momentum vectors), decreasing the volume of the quench region (such as by reducing the distance between the injection port and the outlet), and reducing the temperature of the frusto-conical surface using a temperature control system.

On the other hand, if it is determined that adjustments should be made to decrease the turbulence to a lower turbulence, then the process continues on to step 315*b* where such adjustments are made to the quench chamber in the direction of a low-turbulence configuration. Such adjustments can include, but are not limited to, decreasing the flow rate of the conditioning fluid, decreasing the angle of the frusto-conical surface (thus decreasing the angle between the momentum vectors), increasing the volume of the quench region (such as by increasing the distance between the injection port and the outlet), and increasing the temperature of the frusto-conical surface using a temperature control system.

Whether or not the turbulence of the quench chamber is adjusted, at step 520, a reactor produces a reactive mixture, preferably using a working gas supplied from a working gas supply device and a precursor material supplied from a precursor material supply device. In a preferred embodiment, the working gas flows into the reactor, where energy is delivered to the working gas, thereby forming a plasma. The plasma is applied to precursor material that is flown into the reactor. The combination of the plasma to the precursor material forms the reactive mixture.

At step 530, the reactive mixture flows from the reactor into the quench region of the quench chamber, preferably through an injection port that fluidly couples the quench region to the reactor.

At step 540, conditioning fluid flows into the quench region, preferably through one or more inlets that fluidly couple the quench region to a conditioning fluid supply device or a chamber that temporarily holds the conditioning fluid.

Although the flow chart shows step of the conditioning fluid being flown into the quench region after the step of the reactive mixture being flown into the quench region, it is contemplated that the conditioning fluid can also be flown into the quench region at the same time or before the reactive mixture. Furthermore, the configuration of the quench chamber affects the manner in which the reactive mixture and the conditioning fluid are introduced into the quench region. As discussed above, depending on the degree of turbulence desired, several factors can vary, including, but not limited to, the flow rate of the conditioning fluid, the angle of the frusto-conical surface (and consequently, the angle between the momentum vectors), the volume of the quench region, the distance between the injection port and the outlet, and the temperature of the frusto-conical surface.

At step 550, the conditioning fluid quenches the reactive mixture while the two are combined within the quench region. As previously discussed, the higher the level of turbulence, the higher the quench rate.

The process can then come to an end. Alternatively, the process can repeat back at step 510, where adjustments regarding turbulence level can be made, if appropriate, before producing and quenching a reactive mixture.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A quench chamber comprising:
a frusto-conical body having a wide end, a narrow end, and a quench region formed between the wide end and the narrow end;
a reactive mixture inlet configured to receive a reactive mixture comprising plasma energized precursor material from an output of a plasma reactor and to supply the reactive mixture into the quench region in the direction of the narrow end, wherein the quench region is configured to enable the reactive mixture to expand upon exiting the reactive mixture inlet;
one or more conditioning fluid inlets separated from the reactive mixture inlet and configured to supply a conditioning fluid into the quench region along a plurality of momentum vectors of conditioning fluid that correspond to angles of a frusto-conical surface of the frusto-conical body in the direction of the narrow end via one or more openings different from the reactive mixture inlet, wherein a gap is formed between the reactive mixture inlet and the frusto-conical surface of the frusto-conical body, the gap acting as a channel for supplying conditioning fluid into the quench region, and the frusto-conical surface of the frusto-conical body is configured to produce a turbulent flow within the quench region, thereby promoting the quenching of the reactive mixture with the conditioning fluid to form a cooled gas-particle mixture; and
a gas-particle mixture outlet disposed at the narrow end, the outlet configured to receive the cooled gas-particle mixture from the quench region.

2. The quench chamber of claim 1, wherein the reactive mixture inlet is configured to supply the reactive mixture into the quench region along a first momentum vector, the frusto-conical body is configured to supply the conditioning fluid to the quench region along a second momentum vector, and the second momentum vector has an oblique angle greater than 20 degrees relative to the first momentum vector.

3. The quench chamber of claim 1, wherein the gas-particle mixture outlet is positioned a first distance away from the reactive mixture inlet, the frusto-conical body is positioned at least a second distance away from the reactive mixture inlet, and the first distance is greater than the second distance.

4. The quench chamber of claim 3, wherein the relative positioning of the frusto-conical body and the reactive mixture inlet is adjustable, whereby the first distance and the second distance are adjustable.

5. The quench chamber of claim 1, wherein the one or more conditioning fluid inlets supply conditioning fluid into the quench region to produce a flow having a Reynolds Number of at least 1000.

6. The quench chamber of claim 1, wherein the volume of the quench region is adjustable by adjusting a relative positioning of the frusto-conical surface and the one or more conditioning fluid inlets.

7. The quench chamber of claim 1, wherein the frusto-conical body is configured to supply the conditioning fluid to the quench region along a plurality of momentum vectors, and the angle at which the frusto-conical body supplies the conditioning fluid to the quench region is adjustable by adjusting an angle of the frusto-conical surface.

8. An apparatus for cooling a reactive mixture to condense particle therefrom, the apparatus comprising:
a plasma reactor configured to form the reactive mixture from plasma and a precursor material;
a quench chamber to cool the reactive mixture comprising a frusto-conical body having a wide end, a narrow end, and a quench region formed between the wide end and the narrow end, wherein the quench chamber is configured to receive the reactive mixture from the plasma reactor through a reactive mixture inlet into the quench region, to receive a conditioning fluid from a conditioning fluid supply through one or more fluid supply inlets separated from the reactive mixture inlet, and to flow the conditioning fluid into the quench region, the quench region is configured to enable the reactive mixture to expand upon exiting the reactive mixture inlet, a gap is formed between the reactive mixture inlet and the frusto-conical surface of the frusto-conical body, the gap acting as a channel for supplying conditioning fluid into the quench region, the frusto-conical body is configured to supply the conditioning fluid into the quench region at the same time as the reactive mixture is supplied into the quench region via the reactive mixture inlet and at an angle intersecting the angle at which the reactive mixture is supplied into the quench region in order to produce a turbulent flow within the quench region, thereby promoting the quenching of the reactive mixture with the conditioning fluid to form a cooled gas-particle mixture; and
a suction generator fluidly coupled to an outlet at the narrow end of the frusto-conical body and configured to generate suction at the narrow end to force the cooled gas-particle mixture out of the quench chamber through the outlet.

9. The apparatus of claim 8, wherein the reactive mixture inlet is configured to supply the reactive mixture into the quench region along a first momentum vector, the frusto-conical body is configured to supply the conditioning fluid to the quench region along a second momentum vector, and the second momentum vector has an oblique angle greater than 20 degrees relative to the first momentum vector.

10. The apparatus of claim 8, wherein the outlet is positioned a first distance away from the reactive mixture inlet, the frusto-conical body is positioned at least a second distance away from the reactive mixture inlet, and the first distance is greater than the second distance.

11. The apparatus of claim 10, wherein the relative positioning of the frusto-conical body and the reactive mixture inlet is adjustable, whereby the first distance and the second distance are adjustable.

12. The apparatus of claim 8, wherein the one or more conditioning fluid inlets supply conditioning fluid into the quench region to produce a flow having a Reynolds Number of at least 1000.

13. The apparatus of claim 8, wherein the volume of the quench region is adjustable by adjusting a relative positioning of the frusto-conical surface and the one or more conditioning fluid inlets.

14. The apparatus of claim 8, wherein the frusto-conical body is configured to supply the conditioning fluid to the quench region along a plurality of momentum vectors, and the angle at which the frusto-conical body supplies the conditioning fluid to the quench region is adjustable by adjusting an angle of the frusto-conical surface.

15. The apparatus of claim 8, further comprising a fluid supply element configured to adjust a flow rate of the conditioning fluid into the quench region.

16. The apparatus of claim 8, further comprising a precursor supply device coupled to the plasma reactor, wherein the precursor supply device is configured to supply the precursor material to the plasma reactor in powder form.

* * * * *